United States Patent [19]

Broxterman et al.

[11] 4,118,297
[45] Oct. 3, 1978

[54] FUSED POLY-NUCLEAR AROMATIC CYCLIC SULFONIUM ZWITTERIONS AND POLYMERS THEREOF

[75] Inventors: William E. Broxterman; Demetrius Urchick; Donald L. Schmidt; Clayton W. Hoornstra, all of Midland, Mich.

[73] Assignee: The Dow Chemical Company, Midland, Mich.

[21] Appl. No.: 664,791

[22] Filed: Mar. 8, 1976

[51] Int. Cl.² ............................................. C08G 65/44
[52] U.S. Cl. ......................... 204/159.11; 260/327 TH; 260/332.3 R; 260/332.3 P
[58] Field of Search .................. 260/332.3 R, 332.3 P, 260/327 TH, 47 R, 49; 428/457; 204/159.11

[56] References Cited

U.S. PATENT DOCUMENTS

| | | | |
|---|---|---|---|
| 3,660,431 | 5/1972 | Hatch et al. | 260/332.3 R |
| 3,767,622 | 10/1973 | Hatch et al. | 260/47 R |
| 3,915,991 | 10/1975 | Schmidt et al. | 260/329 S |

Primary Examiner—Lester L. Lee

[57] ABSTRACT ar-Cyclic sulfonium, fused polynuclear areneoxides exemplified by the structural formula:

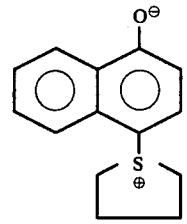

polymerize readily upon exposure to ultraviolet light and/or heat to yield water-insoluble resins useful as adhesives, coatings, films and the like. Fused polynuclear zwitterions containing more than one areneoxide and cyclic sulfonium group per molecule crosslink under such conditions.

18 Claims, No Drawings

FUSED POLY-NUCLEAR AROMATIC CYCLIC SULFONIUM ZWITTERIONS AND POLYMERS THEREOF

BACKGROUND OF THE INVENTION

This invention relates to ar-cyclic sulfonium areneoxides and polymers thereof.

The propensity of many sulfonium salts to polymerize upon exposure to heat to yield a polyester and a by-product sulfide has been recognized by Hatch in Canadian Pat. No. 708,230, Lloyd in U.S. Pat. No. 3,409,660 and Kangas in U.S. Pat. No. 3,322,737. More recently in U.S. Pat. Nos. 3,636,052, 3,660,431, 3,723,386 and 3,749,737, it has been recognized that various hydroxyphenyl cyclic sulfonium salts may be converted to phenoxide cyclic sulfonium zwitterions that polymerize readily upon exposure to heat without yielding sulfide by-products.

Heretofore, the polymerization of phenoxide cyclic sulfonium zwitterions by exposure to radiative energy has not been disclosed.

SUMMARY OF THE INVENTION

The present invention, in one aspect, resides in a novel group of cyclic sulfonium zwitterions that polymerize very readily upon exposure to radiative energy without forming sulfide by-products. Specifically, the members of this novel group are ar-cyclic sulfonium, fused polynuclear areneoxides, generally represented by the structural formula:

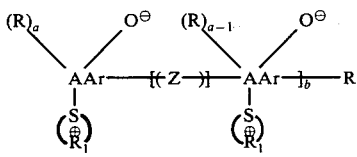

wherein AAr is a fused cyclic polynuclear aromatic polyyl, Ar is cyclic aromatic polyyl which may be mononuclear or fused polynuclear, each R is independently a suitably inert monovalent radical capable of existing as a ring substituent on AAr or Ar, each $R_1$ is independently a suitably inert divalent organic radical capable of forming a heterocyclic ring with divalent sulfur, each Z is independently a suitably inert divalent radical capable of bridging AAr and Ar, $a$ is a positive number corresponding to the number of remaining available ring positions on AAr or Ar, $b$ is 0 or a positive number, and $c$ is 0 or 1. For the purpose of this invention, the term "aromatic polyyl" means a polyvalent (more than 1) aromatic radical having at least one aromatic carbocyclic ring. For example, benzene as a polyyl has a maximum valence of six, the maximum valence of a naphthalene polyyl is eight and the maximum valence of a polyyl of anthracene is 10. The term "fused polynuclear cyclic aromatic polyyl" means a polyvalent aromatic radical having at least two aromatic rings sharing a pair of carbon atoms wherein at least one of the rings is carbocyclic. By a "suitably inert radical" is meant a radical that is inert to the cyclic sulfonium moiety and the areneoxide moiety and does not prevent polymerization of the zwitterion through the cyclic sulfonium moiety.

Surprisingly, the zwitterions of this invention which are characterized by the presence of a fused aromatic ring stucture bearing an anionic oxide and a cationic cyclic sulfonium group polymerize upon exposure to radiative energy at greater rates and at lower temperatures than do similar zwitterions that do not contain a fused aromatic ring. If the zwitterion contains an average of more than one anionic oxide and cyclic sulfonium group per molecule, i.e., $b = 1$ or more, crosslinking occurs through these additional groups.

A second aspect of this invention resides in the polymers formed by polymerization of the aforementioned zwitterions. Such polymers are characteristically formed by a ring-opening reaction between the arene oxide moiety and the cyclic sulfonium group to form thioorganooxy linkages represented by the formula $—SR_1O—$.

Solid polymer films and hard surface, adherent coatings exhibiting good impact resistance and resistance to water and various alcohols are obtained by applying the crosslinkable zwitterions to surfaces of substrate, e.g., metal substrates, and thereafter subjecting it to conditions conducive to polymerization. In addition, the aforementioned zwitterions may be combined with conventional cyclic sulfonium zwitterions, e.g., those disclosed in U.S. Pat. Nos. 3,636,052 and 3,660,431, and then copolymerized using radiative and/or thermal means. The zwitterions of the present invention are also useful in the applications described in U.S. Pat. Nos. 3,901,816, 3,900,619, 3,836,385, and 3,804,797.

DETAILED DESCRIPTION OF PARTICULAR EMBODIMENTS

In fused polynuclear zwitterions of particular interest, AAr, as depicted in the aforementioned formula, is a fused polynuclear aromatic carbocyclic or aromatic carbocylic/(N, O or S) aromatic heterocyclic polyyl. An aromatic carbocyclic/(N, O or S) aromatic heterocyclic polyyl is one having at least one aromatic carbocyclic ring fused with one or more five or six membered aromatic heterocyclic rings, each heterocyclic ring containing only one of —N—, —S— or —O—, provided that the heterocyclic ring containing —N— is a six-membered ring similar to pyridine. Examples of suitable carbocyclic/heterocyclic polyyls include polyyls of quinoline, isoquinoline, acridine, benzoquinoline, 1-azophenanthrene, benzofuran, benzothiophene, and the like. Preferably, AAr is a fused polynuclear arenepolyyl, e.g. polyyls of naphthalene, anthracene, and phenanthrene. An especially preferred polynuclear arenepolyyl is the polyyl of naphthalene.

Ar is a mononuclear aromatic carbocyclic polyyl or AAr as defined hereinbefore. An exemplary mononuclear polyyls is the polyyl of benzene. Preferably, Ar is AAr as defined hereinbefore, especially the polyyl of naphthalene.

R is a suitably inert monovalent radical which is capable of existing as a substituent on AAr or Ar. Examples include H, X wherein X is halogen such as Cl or Br, OH, R', —OR', —SR',

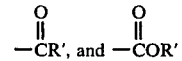

wherein R' is hydrocarbyl or substituted hydrocarbyl. Hydrocarbyl is a monovalent hydrocarbon radical having 1 to 20 carbons, preferably alkyl, cycloalkyl, alkenyl, aryl, alkylaryl, aralkyl and similar hydrocarbon radicals having 1 to 8 carbons. Exemplary substituents of substituted hydrocarbyl include X, OH, —OR', —SR' and the like wherein X and R' are as defined hereinbefore. Preferably R is hydrogen, hydroxyl, $C_1$–$C_8$ alkyl, and $C_1$–$C_8$ alkoxy, with hydrogen and $C_1$–$C_4$ alkyl being especially preferred. It should be noted, however, that the presence of hydroxyl and similar electron releasing substituents on AAr or Ar tends to decrease the activity of the zwitterion toward polymerization. Moreover, the use of R groups other than hydrogen, particularly very bulky ones such as higher hydrocarbyls, e.g., those having more than 4 carbons, and ring deactivating groups such as halogen should be limited as necessary to insure formation of a stable ar-cyclic sulfonium fused polynuclear arene oxide. While R groups may be in any available ring position on AAr and Ar, the R groups other than hydrogen, particularly those R groups more bulky than methyl are usually in the 3-, 6- or 7-positions when AAr or Ar is naphthalene polyyl with positions identified as follows:

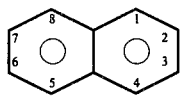

In the zwitterions of this invention, the cyclic sulfonium moiety,

is advantageously a 5- to 7-membered heterocyclic ring that is most often a ring substituent of the same carbocyclic aromatic ring bearing the anionic oxide moiety. Preferably, the cyclic sulfonium moiety is a 5- or 6-membered ring usually substituted in a ring position on AAr or Ar that is ortho or para to the anionic oxide moiety. For example, when AAr or Ar is the polyyl of naphthalene, the cyclic sulfonium moiety is likely to be in the 4-position when the anionic oxide is in the 1-position and in the 1- or 3-position when the anionic oxide is in the 2-position. It should be noted, however, that the cyclic sulfonium moiety is sometimes substituted in the 6-position, particularly when the anionic oxide is in the 2-position and 1-position is not available for substitution. Of the preferred cyclic sulfonium moieties, the 5-membered rings are especially preferred.

$R_1$ is any suitably inert divalent organic radical that can exist in a heterocyclic ring containing sulfur. Of course, $R_1$ should not contain bulky and/or reactive groups that would (1) prevent the formation of the stable cyclic sulfonium moiety on AAr or Ar or (2) deleteriously affect the ability of the zwitterion to polymerize. Accordingly, $R_1$ is most advantageously hydrocarbylene or substituted hydrocarbylene wherein hydrocarbylene is a divalent hydrocarbon radical. Alternatively, $R_1$ is suitably heterohydrocarbylene or substituted heterohydrocarbylene wherein the chain of the hydrocarbon is interrupted by a hetero atom, e.g., oxygen or sulfur. Hydrocarbylene and heterocarbylene are of sufficient length to provide a 5- to 7-membered ring including

In all suitable $R_1$, the two carbons of $R_1$ bonded to

are methylene. Thus, steric problems which might hinder formation of the zwitterion or polymerization thereof are reduced. Exemplary suitable hydrocarbylenes and heterohydrocarbylenes include alkylene, cycloalkylene, alkenylene, alkylenearylenealkylene, alkyleneoxyalkylene, and alkylenethioalkylene. When $R_1$ is substituted hydrocarbylene or substituted heterohydrocarbylene, suitable substituents include monovalent radicals given in the definition of R such as OH, R', OR', and —SR' wherein R' is hydrocarbyl. Preferably, $R_1$ is a hydrocarbylene such as —$(CH_2)_4$—, —$(CH_2)_5$—, $$-CH_2CHCH_2CH_2-$$
$$\phantom{-CH_2CH}|\phantom{CH_2CH_2-}$$
$$\phantom{-CH_2CH}R_2\phantom{CH_2CH_2-}$$

wherein $R_2$ is $C_1$–$C_4$ alkyl or aryl, such as phenyl or alkoaryl such as tolyl,

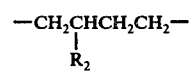

or heterohydrocarbylene such as —$(CH_2)_2$—O—$(CH_2)_2$—, with —$(CH_2)_4$— and $$-CH_2CHCH_2CH_2-$$
$$\phantom{-CH_2CH}|\phantom{CH_2CH_2-}$$
$$\phantom{-CH_2CH}R_2\phantom{CH_2CH_2-}$$

being especially preferred.

Z is a suitably inert divalent radical capable of bridging aromatic rings each bearing ring-substituted oxide anion and cyclic sulfonium cation. Suitable examples of Z include —O—, —S—,

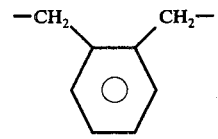

—$R_3$—, —O$R_3$O—, —S$R_3$S—, —$R_3$O—, —$R_3$S—,

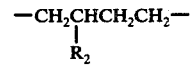

and the like wherein $R_3$ is hydrocarbylene or substituted hydrocarbylene with substituents as defined for R. Advantageously, $R_3$ is hydrocarbylene having 1–8, especially 2–4, carbons. Preferably, Z is —S—, —O—, alkylene, arylene, or oxyalkyleneoxy. Especially preferred are —O($C_mH_{2m}$)O—,

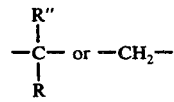

wherein $m = 1-4$ and $R'' = C_1-C_4$ alkyl.

Some of the most preferred zwitterions of this invention are those represented by the structural formula:

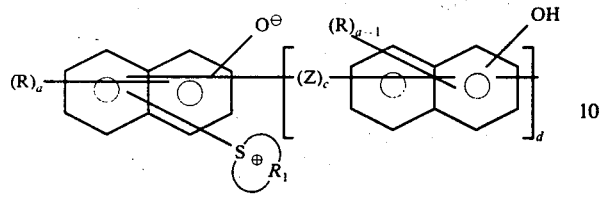

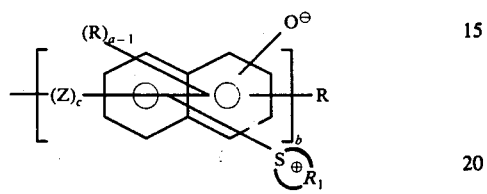

wherein each R, $R_1$, and Z are independently as defined hereinbefore. In the foregoing most preferred zwitterions $a$ is 5 or 6, $c$ is 0 or 1, preferably 1, and the sum of $b$ and $d$ is 0 or a positive number. While $b + d$ may be any number from one up to the highest number of ar-hydroxynaphthalenes that can be bonded together in a linear fashion by direct linkage of naphthalene groups, i.e., when $c = 0$, or through Z linkages. Depending on the particular Z linkage, $b + d$ may be as high as 20, but, is rarely greater than 5 and most often no more than 1. It is generally preferable that the ratio of $b$ to $d$ be at least 1. Most advantageously, when Z is $-O(C_mH_{2m})O-$ or

as defined hereinbefore, $b + d$ is preferably 1. When Z is $-CH_2-$, $b + d$ is 1-20, preferably 1-5.

Examples of the most preferred zwitterions are represented by the formulas:

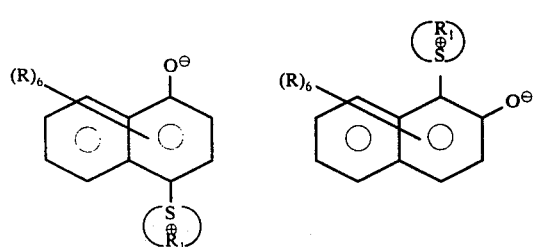

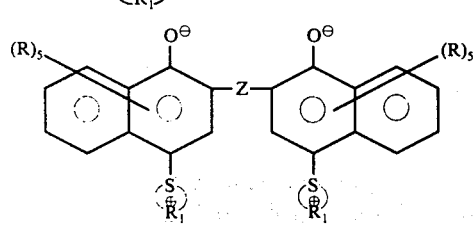

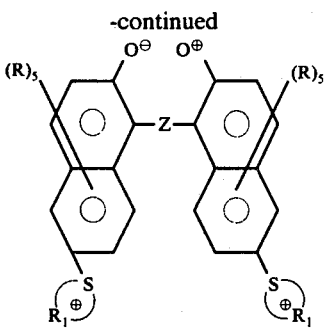

wherein each R is independently H, OH, $C_1-C_8$ alkyl or $C_1-C_8$ alkoxy provided that no more than one R group per

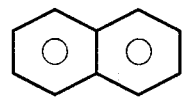

is OH or $C_1-C_8$ alkoxy; each $R_1$ is independently $-(CH_2)_4-$, $-(CH_2)_5-$,

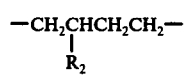

wherein $R_2$ is $C_1-C_8$ alkyl, aryl such as phenyl or alkaryl such as tolyl

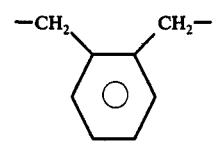

or $-(CH_2)_2-O-(CH_2)_2-$; Z is $-O(C_mH_{2m})O-$ wherein $m = 1-6$,

wherein $R''$ is $C_1-C_4$ alkyl, or $-CH_2-$. Preferably in the aforementioned formulas, each R is independently H or $C_1-C_4$, especially H; each $R_1$ is independently $-(CH_2)_4-$ or

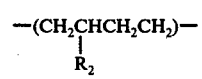

wherein $R_2$ is $C_1-C_4$ alkyl; and Z is $-O(C_mH_{2m})O-$ wherein $m = 2-4$,

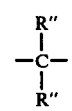

wherein $R''$ is methyl, or $-CH_2-$.

The zwitterions of the present invention are prepared by first preparing the appropriate hydroxyarylene cyclic sulfonium salt, hereinafter called salt, and converting the salt to the zwitterion.

As a general rule, the salt is most advantageously prepared by one of the following processes:

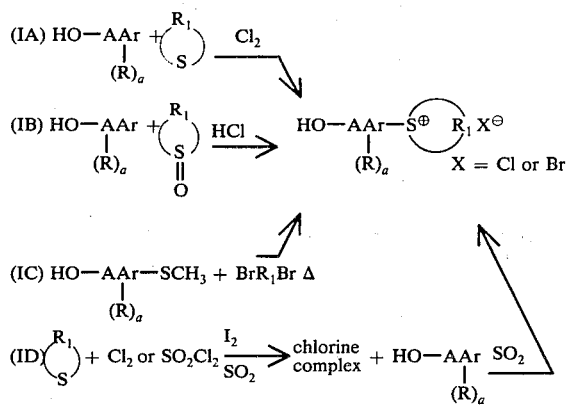

wherein AAr, R, R₁ and a are as defined hereinbefore. These processes require that HO—AAr—(R)$_a$ have at least one active ring hydrogen per intended cyclic sulfonium group. Accordingly, the foregoing processes IA, IB and ID are not as advantageously employed if R is a strong electron withdrawing group such as halogen. Such sulfonium salts are more advantageously prepared by Process IC or by first forming the sulfonium salt as in Processes IA and IB and subsequently substituting the desired electron withdrawing group on the aromatic ring. To prepare the sulfonium salts having more than one sulfonium group per molecule, it is most desirable to substitute a polyphenol having the formula:

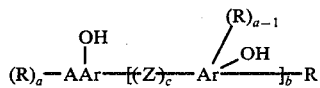

for HO—AAr—(R)$_a$ in the aforementioned processes, preferably Process ID.

In Process IA the arenol and cyclic sulfide react at −40° C. to 0° C. in the presence of chlorine to give moderate 30–40% yields of the aromatically substituted cyclic sulfonium chloride.

In Process IB the arenol and cyclic sulfoxide condense in the presence of a strong anhydrous acid such as HCl. Methanol can be used as a solvent. Low temperatures and a Lewis acid catalyst such as AlCl₃, SO₂, etc. are useful in minimizing side reactions and dark products.

Process IC involving the reaction of the alkylthioarenol and the terminally substituted organodihalide such as 1,4-dichlorobutane or 1,5-dibromopentane at an elevated temperature, normally about 100°–200° C., is applicable with many substituted arenols and a variety of dihalides. Normally excess dihalide is used as a diluent and recovered along with the by-product alkyl halide.

In process ID, the cyclic sulfide,

is contacted at −50° to 10° C. in a liquid sulfur dioxide solution with a minor amount, e.g., up to about 0.002 mole per mole of

of iodine and hydrogen chloride to form a chlorine complex believed to correspond to the formula

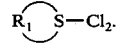

Generally the hydrogen chloride is employed in an amount sufficient to essentially saturate the sulfur dioxide solution. The resulting chlorine complex is then contacted in liquid sulfur dioxide with the desired arenol at −50° C. to 10° C. in the presence of a catalytic amount of a Lewis acid such as boron trifluoride. The reactions of process ID are most advantageously carried out using stoichiometric amounts of the reactants. The resulting sulfonium salt is then advantageously recovered as a water solution by adding water to the reaction mixture and then removing the volatile sulfur dioxide.

Alternatively the desired sulfonium salt is prepared by the process disclosed in detail in British Pat. No. 1,235,815. The process involves the reaction of a polynuclear quinone such as

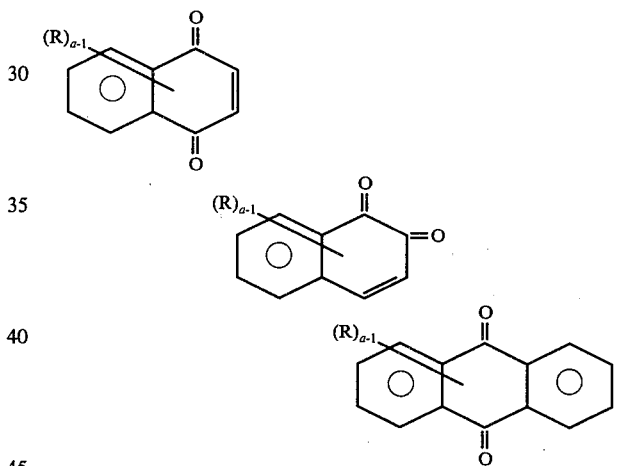

with the appropriate cyclic sulfide in a strongly acid medium, i.e., having a pH below 1 such as 60–85% aqueous sulfuric acid, and at temperatures from −15° to 25° C. The practice of this process yields a sulfonium salt having at least 2 ring-substituted hydroxyl groups per sulfonium groups as exemplified by the following chemical reaction:

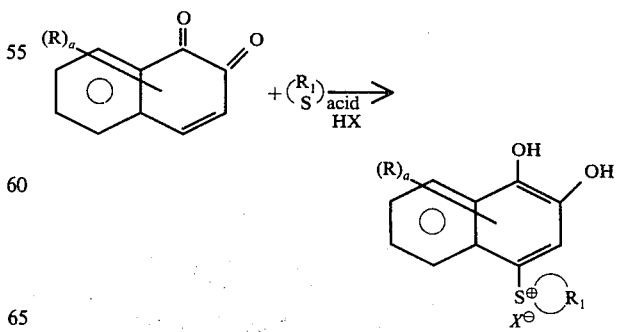

The aforementioned cyclic sulfonium salts having a non-basic inorganic anion such as chloride, bromide, perchlorate or bisulfate are generally stable, crystalline salts at room temperature. They are soluble in polar hydroxylic solvents such as water, methanol and isopropanol. Stable mono- or di-hydrates have been isolated of some chlorides.

Purification of the salts can be achieved by crystallization from a mixed solvent as acetone or ether methanol, by conversion into an insoluble salt, e.g., perchlorate, or by precipitation from aqueous solution with a precipitant diluent such as dioxane, tetrahydrofuran or higher alcohol.

Conversion of the aforementioned sulfonium salt into the desired reactive zwitterion is achieved by known methods. Ion-exchange with an anion-exchange resin in hydroxide form is particularly suitable. For some salts direct treatment with a strong inorganic base in a solvent such as anhydrous alcohol, in which the by-product inorganic salt has limited solubility, is preferred.

The cyclic sulfonium zwitterion frequently is obtained as a stable crystalline hydrate. For example, the 4-tetrahydrothiophenium naphth-1-oxide zwitterion containing one molecule of water per 2 molecules of the zwitterion is obtained at room temperature in the form of a crystalline solid. Attempts to remove the water of hydration of this zwitterion by vacuum drying at room temperature result in polymerization.

Polymerization of the foregoing zwitterion is readily achieved by the thermal conditions employed in the polymerization of phenoxide cyclic sulfonium zwitterions of U.S. Pat. No. 3,723,386. More importantly, polymerization of zwitterions of this invention is most readily effected by subjecting them to radiative energy characteristic of ultra violet light, and similar actinic radiations which are absorbed by fused polynuclear aromatic compounds.

Preferably, the type of radiation is an ultra violet type emitted from an artificial source capable of providing electro-magnetic radiation having a wavelength in the range from about 3000 to about 4000 Å. An exposure time to the ultra violet light in the range from about 2 to about 60 seconds is preferably employed to effect polymerization. Generally, the source of radiation is positioned from about 6 to about 36 inches from the zwitterion being polymerized. Suitable radiation may be readily obtained from such sources as sunlight, mercury vapor discharge lamps, fluorescent lamps, carbon arcs, etc. It is understood that particular conditions will vary depending upon the source, distance, etc. Accordingly, proper time of radiation is best determined by a few trials.

The resulting polymers are generally characterized as containing a plurality of —SR$_1$O— linkages. Most polymers of such zwitterions exhibit physical characteristics similar to those described in U.S. Pat. No. 3,660,431. Copolymers can be made from mixtures of two or more sulfonium monomers either blended as finely ground solids or in solution. In general the copolymer properties are intermediate between those of the corresponding homopolymers.

Once polymerized, products can be fabricated from the polymer in conventional ways. Alternately, the zwitterion can be placed in a mold and polymerized in situ. Films can be cast from solutions of the cyclic sulfonium zwitterions in water or other polar solvents such as methanol, methanol-acetone mixtures, dimethyl sulfoxide, etc.

The following examples are given to illustrate the invention and should not be construed as limiting its scope. Unless otherwise indicated, all parts and percentages are by weight.

EXAMPLE 1

A. Preparation of 4-(1-Hydroxynaphthyl)tetrahydropthiophenium Chloride

Into a solution of 36.6 g (0.416 mole) of tetrahydrothiophene in 200 ml of methylene chloride is introduced 29.5 g (0.416 mole) dry chlorine gas while maintaining the temperature of the solution at −50° C. with a dry ice bath. The chlorine gas is added continuously over a period of ½ hours. To the resulting yellow reaction mixture is slowly added a solution of 60.1 g (0.416 mole) of α-naphthol in 200 ml methylene chloride/50 ml methanol. The temperature of the mixture is then allowed to rise to 0° C. while the mixture is stirred. After 2 hours, the methylene chloride solvent is removed under vacuum at a temperature of 20° C. A 400-ml portion of acetone is added to the residual product and then removed under vacuum. Acetone is again added to the solid, and the solid is filtered. The product is recovered as a crystalline solid (~60g).

B. Conversion of the Sulfonium Salt to Zwitterion

The sulfonium salt is dissolved in methanol and passed through a wet, strong base anion-exchange resin until a pH of about 10.5 is reached. The product is recovered by conventional means as described in U.S. Pat. No. 3,636,052. Examination of the product by chemical and spectral analysis indicates a zwitterion having the following structure:

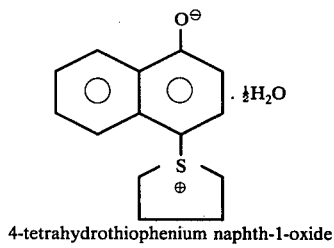

4-tetrahydrothiophenium naphth-1-oxide

C. Polymerization

A solution of 30% of the aforementioned zwitterion in methanol is applied as a 0.2 mil (0.005 mm) coating onto a glass slide using a wire wound rod. The coating is dried at 22° C. for ~1 hour. The dried coating is then exposed to a 140 amp (4000 watt) carbon arc lamp at a distance of 24 inches for a period of time as indicated in Table I. Interposed between the lamp and the slide are a Pyrex glass filter to block radiation of wavelength less than 3000 Å and a heat filter cell containing distilled water to remove substantially all infrared radiation, e.g., radiation having wavelength greater than 8000 Å. During the exposure, a cool air stream is passed over the coated side to prevent the temperature of the slide from increasing to 50° C. Subsequently, the radiated slide is placed in water at room temperature and agitated for 1 minute. The water resistance of the coating is observed and the results are recorded in Table I.

For purposes of comparison, coatings of other zwitterions and mixtures thereof are similarly coated on glass slides, radiated and tested for water resistance. The results of these tests are also recorded in Table I.

TABLE I
| Sample No. | Zwitterion type | wt % | Exposure time (1), sec. |
|---|---|---|---|
| 1 | 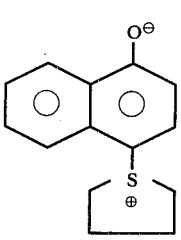 | 100 | 2.5 |
| 2 | 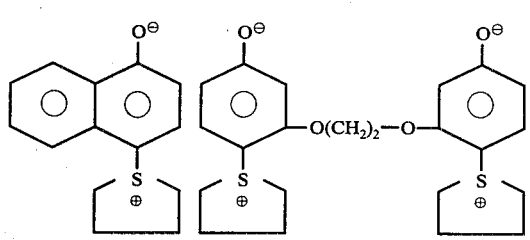 | 90/10 | 5 |
| 3 | 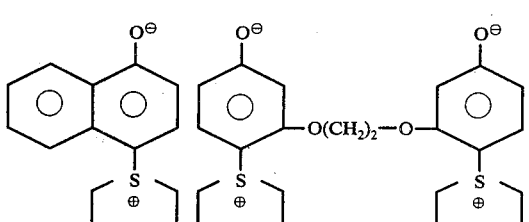 | 95/5 | 5 |
| C₁* | 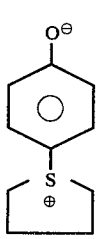 | 100 | 15 |
| C₂* | 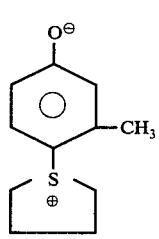 | 100 | 15 |
| C₃* | 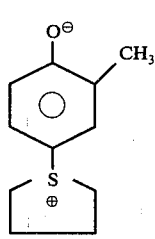 | 100 | 20 |

TABLE I-continued

| Sample No. | Zwitterion type | wt % | Exposure time (1), sec. |
|---|---|---|---|
| C$_4$* | 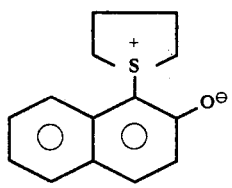 | 100 | 60 |

*Not an example of this invention
(1) Minimum exposure time in seconds required to produce a coating that will not dissolve upon soaking in cool water.

As evidenced by the foregoing data, the polynuclear aromatic cyclic sulfonium zwitterions of the present invention cure at much faster rates than do similar mononuclear zwitterions.

EXAMPLE 2

A. Preparation of 4-(2-hydroxynaphthyl)tetrahydrothiophenium Chloride

Following the general procedure of Example 1, Part A, tetrahydrothiophene is reacted with β-naphthol to form the aforementioned salt.

B. Conversion to 1-Tetrahydrothiophenium Naphth-2-oxide

Following the procedure of Example 1, part B, the cyclic sulfonium chloride is converted to its corresponding zwitterion represented by the formula:

C. Polymerization

A solution of 10–15% of the aforementioned zwitterion in methylene chloride is applied as a 0.1–0.2 mil (~0.004 mm) dried coating onto a sheet of an aluminum alloy using a wire wound rod. The coating is dried at room temperature for 16 hours. The dried coating is then exposed through a negative to an ultraviolet light source consisting of six 36 watt fluorescent lamps at distance of 2 inches for various periods of time as specified in Table II. The exposed samples are then swabbed with a saturated aqueous solution of crystal violet dye, rinsed with water and air dried. The dried samples are placed in water at room temperature and are then agitated for 1 minute. The water resistance of each coated sample is measured by observing the retention of the dye image, and the results are recorded in Table II.

TABLE II

| Sample No. | Exposure Time, min. | Dye Image (1) |
|---|---|---|
| 1 | 1/12 | None |
| 2 | 1/4 | Faint |
| 3 | 1/2 | Medium Visible |
| 4 | 1 | Complete Retention |
| 5 | 2 | " |
| 6 | 4 | " |
| 7 | 6 | " |
| 8 | 8 | " |

(1) Visual observation of the amount of dye retained.

EXAMPLE 3

Following the conditions of ultraviolet light exposure of Example 2, the cyclic sulfonium zwitterion of Example 1 similarly polymerizes to form a water resistant coating after an exposure time of 25–30 seconds.

What is claimed is:

1. A polymerizable ar-cyclic sulfonium, fused polynuclear areneoxide represented by the formula:

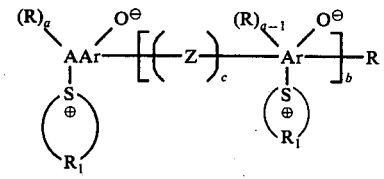

wherein AAr is a fused cyclic polynuclear aromatic polyyl, each Ar is independently a cyclic aromatic polyyl, each R is independently a suitably inert monovalent radical capable of existing as a ring substituent on AAr or Ar, each R$_1$ is independently a suitably inert divalent organic radical capable of forming a heterocyclic ring containing sulfur, each Z is independently a suitably inert divalent radical bridging AAr and Ar, each $a$ is independently a positive number corresponding to the number of remaining available ring positions on AAr or Ar, $b$ is 0 or a positive number and $c$ is 0 or 1, said polynuclear areneoxide capable of polymerizing upon exposure to radiative energy at a rate faster than the rate of polymerization of a similar mononuclear areneoxide having only mononuclear aromatic polyyl(s).

2. The areneoxide of claim 1 wherein AAr is a polyyl of naphthalene, anthracene or phenanthrene; each Ar is independently of polyyl of benzene, naphthalene, anthracene or phenanthrene; each R is independently H, Cl, Br, OH, —OR' or —SR' wherein R' is hydrocarbyl or substituted hydrocarbyl wherein each substituent is independently Cl, Br, OH, —OR' or —SR';

is a 5- or 6-membered heterocyclic ring that is a ring substituent of the same carbocyclic aromatic ring of AAr and Ar bearing —O⊖; each $R_1$ is independently hydrocarbylene, heterohydrocarbylene wherein the chain of the hydrocarbon chain of the heterohydrocarbylene is interrupted by oxygen or sulfur or substituted forms thereof wherein each substituent of $R_1$ is independently a monovalent radical equivalent to R provided that $R_1$ has two terminal methylene carbons bonded to the

each Z is independently —O—, —S—,

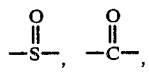

—$R_3$—, —O$R_3$O—, —S$R_3$S—, —$R_3$O—, —$R_3$S—, and

wherein $R_3$ is hydrocarbylene or substituted hydrocarbylene wherein each substituent of $R_3$ is independently a monovalent radical equivalent to R and b is 0–5.

3. The areneoxide of claim 1 represented by the formula

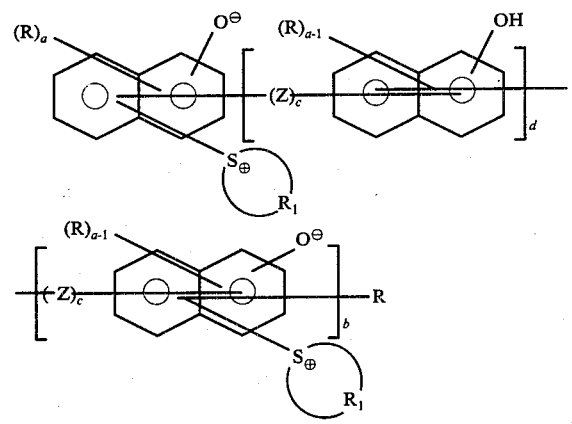

wherein each R is independently H, OH, $C_1$–$C_8$ alkyl, or $C_1$–$C_8$ alkoxy;

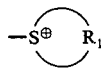

is substituted in a ring position that is ortho or para to —O⊖; each $R_1$ is independently alkylene, alkyleneoxyalkylene or substituted alkylene wherein each substituent is independently OH, R′ or OR′ wherein R′ is alkyl provide that the terminal carbons of $R_1$ are methylene;

each Z is independently —O—, —S—, —O($C_mH_{2m}$)O—, —CH$_2$— or

wherein R″ is $C_1$–$C_4$ alkyl and m = 1 to 4; a is 5 or 6; b + d = 0–5; and c = 0 or 1.

4. The areneoxide of claim 3 wherein each R other than hydrogen is $C_1$–$C_4$ alkyl or OH.

5. The areneoxide of claim 3 wherein each R is hydrogen.

6. The areneoxide of claim 2 represented by one of the following formulas:

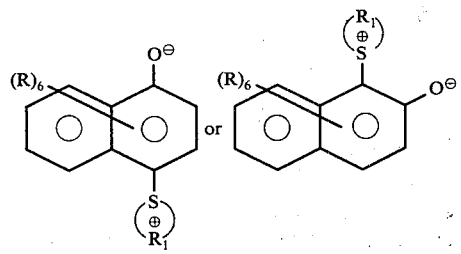

wherein each R is independently H, OH, $C_1$–$C_8$ alkyl or $C_1$–$C_8$ alkoxy provided that no more than one R group is OH or $C_1$–$C_8$ alkoxy and $R_1$ is —(CH$_2$)$_4$—, —(CH$_2$)$_5$—, wherein $R_2$ is $C_1$–$C_8$ alkyl or phenyl,

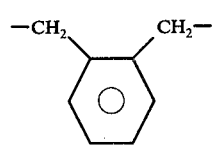

or —(CH$_2$)$_2$—O—(CH$_2$)$_2$—.

7. The areneoxide of claim 6 wherein each R is independently H or $C_1$–$C_4$ alkyl and $R_1$ is —(CH$_2$)$_4$— or

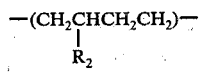

wherein $R_2$ is $C_1$–$C_4$ alkyl.

8. The areneoxide of claim 7 wherein five R groups are H and the remaining R group is H or methyl and $R_1$ is —(CH$_2$)$_4$—.

9. The areneoxide of claim 6 represented by one of the following formulas:

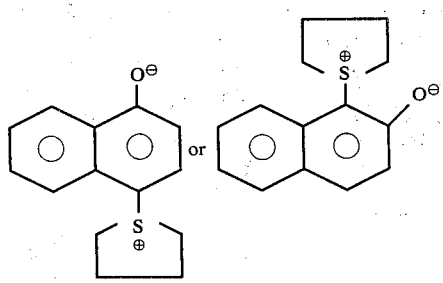

10. The areneoxide of claim 1 represented by one of the following formulas:

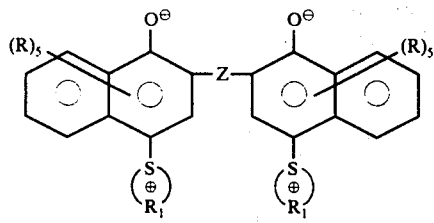

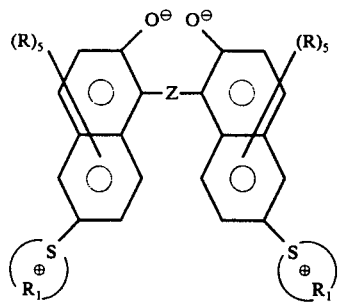

wherein each R is independently H, OH, $C_1$-$C_8$ alkyl or $C_1$-$C_8$ alkoxy provided that no more than one R group per

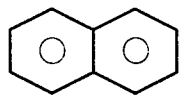

is OH or $C_1$-$C_8$ alkoxy; each $R_1$ is independently —$(CH_2)_4$—, —$(CH_2)_5$—,

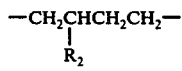

wherein $R_2$ is $C_1$-$C_8$ alkyl or phenyl,

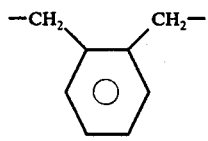

or —$(CH_2)_2$—O—$(CH_2)$—; Z is —O($C_mH_{2m}$)O— wherein m = 1-6 or

wherein R" is H or $C_1$-$C_4$ alkyl.

11. The areneoxide of claim 10 wherein each R is independently H or $C_1$-$C_4$ alkyl and each $R_1$ is independently —$(CH_2)_4$— or

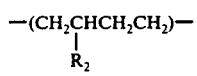

wherein $R_2$ is $C_1$-$C_4$ alkyl.

12. The areneoxide of claim 10 represented by one of the following formulas

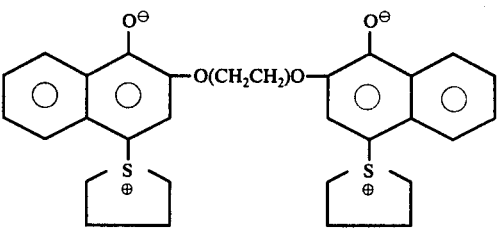

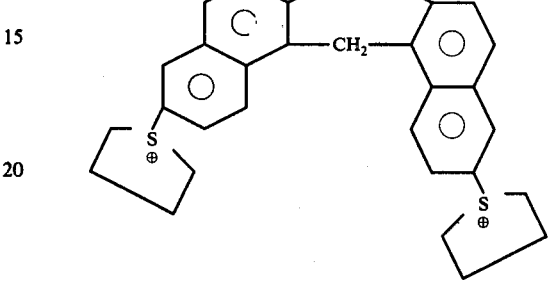

13. The areneoxide of claim 1 wherein each R is independently H, Cl, Br, OH, —OR' or —SR' wherein R' is hydrocarbyl or substituted hydrocarbyl wherein each substituent is independently Cl, Br, OH, —OR' or —SR';

is a 5- or 6-membered heterocyclic ring that is a ring substituent of the same carbocyclic aromatic ring of AAr and Ar bearing —$O^\ominus$; each $R_1$ is independently hydrocarbylene, heterohydrocarbylene wherein the chain of the hydrocarbon chain of the heterohydrocarbylene is interrupted by oxygen or sulfur or substituted forms thereof wherein each substituent of $R_1$ is independently a monovalent radical equivalent to R provided that $R_1$ has two terminal methylene carbons bonded to the

each Z is independently —O—, —S—,

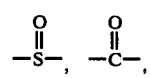

—$R_3$—, —$OR_3O$—, —$SR_3S$—, —$R_3S$—, and

wherein $R_3$ is hydrocarbylene or substituted hydrocarbylene wherein each substituent of $R_3$ is independently a monovalent radical equivalent to R.

14. A polymer prepared by polymerizing by exposure to radiative energy the areneoxide of claim 1.

15. A solid polymer obtained by exposing the areneoxide of claim 6 to ultraviolet radiation.

16. A solid polymer obtained by exposing the areneoxide of claim 10 to ultraviolet light.

17. The polymer of claim 15 in the form of a solid polymer film.

18. The solid polymer film of claim 17 bonded to a metal substrate.

* * * * *

UNITED STATES PATENT AND TRADEMARK OFFICE
CERTIFICATE OF CORRECTION

PATENT NO. : 4,118,297

DATED : October 3, 1978

INVENTOR(S) : William E. Broxterman; Demetrius Urchick; Donald L. Schmidt; Clayton W. Hoornstra It is certified that error appears in the above-identified patent and that said Letters Patent are hereby corrected as shown below:

Column 1, line 35, delete the formula and insert

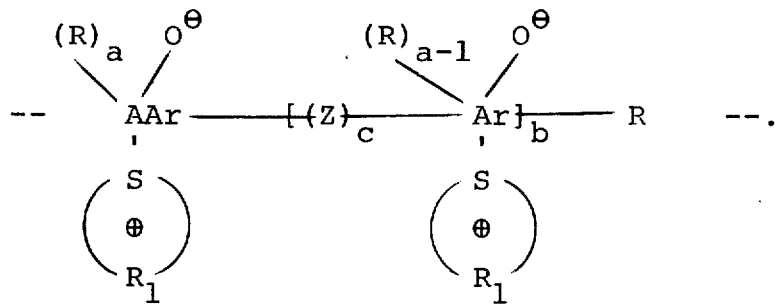

Column 1, line 68, delete "stucture" and insert --structure--.

Column 4, line 37, delete the formula and insert

-- $-CH_2CH_2CH_2CH_2-$ --.
      $|$
      $R_2$

Column 4, line 65, delete "$-\overset{R''}{\underset{R}{C}}-$" and insert -- $-\overset{R''}{\underset{R''}{C}}-$ --.

Column 6, lines 5-10, delete the formula and insert

UNITED STATES PATENT AND TRADEMARK OFFICE
CERTIFICATE OF CORRECTION

PATENT NO. : 4,118,297
DATED : October 3, 1978
INVENTOR(S) : William E. Broxterman; Demetrius Urchick; Donald L. Schmidt; Clayton W. Hoornstra It is certified that error appears in the above-identified patent and that said Letters Patent are hereby corrected as shown below:

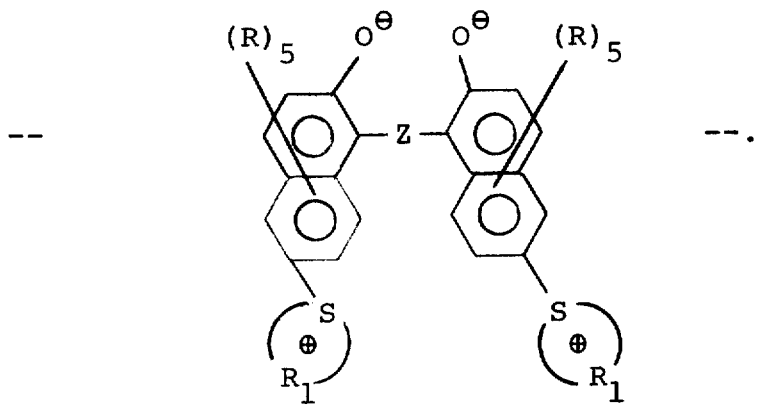

Column 6, line 16, delete "$C_{1-c8}$" and insert --$C_1$-$C_8$--.

Column 7, line 10, delete the formula and insert

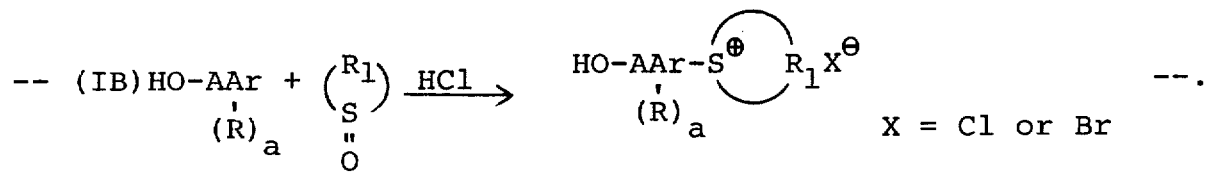

Column 9, line 7, after "solvent" insert --such--.

Column 10, line 6, delete "4-(1-Hydroxynaphthyl)tetrahydropthiophenium" and insert --4-(1-Hydroxynaphthyl)tetrahydrothiophenium--.

Column 13, lines 35-40, delete the formula and insert

UNITED STATES PATENT AND TRADEMARK OFFICE
CERTIFICATE OF CORRECTION

PATENT NO. : 4,118,297

DATED : October 3, 1978

INVENTOR(S) : William E. Broxterman; Demetrius Urchick; Donald L. Schmidt; Clayton W. Hoornstra It is certified that error appears in the above-identified patent and that said Letters Patent are hereby corrected as shown below:

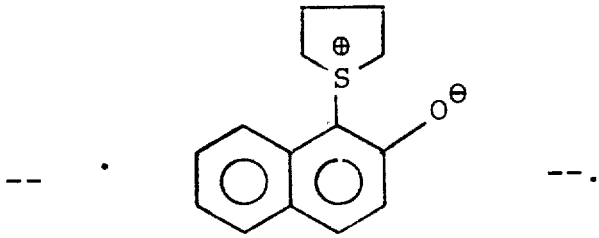

Column 16, line 32, after ")$_5$-," insert -- -CH$_2$CHCH$_2$CH$_2$- --.
$\qquad\qquad\qquad\qquad\qquad\qquad\qquad\qquad\qquad\qquad\quad$ R$_2$ Signed and Sealed this Seventeenth Day of April 1979

[SEAL]

Attest:

RUTH C. MASON
Attesting Officer

DONALD W. BANNER
Commissioner of Patents and Trademarks